(12) United States Patent
Gilan

(10) Patent No.: US 6,506,144 B1
(45) Date of Patent: Jan. 14, 2003

(54) UNIVERSAL PULLBACK MECHANISM FOR IN-SITU TREATMENT DEVICE

(75) Inventor: Ziv Gilan, Kfar Harif (IL)

(73) Assignee: X-Technologies, Ltd., Orangeburg, NY (US)

( * ) Notice: Subject to any disclaimer, the term of this patent is extended or adjusted under 35 U.S.C. 154(b) by 39 days.

(21) Appl. No.: 09/710,963

(22) Filed: Nov. 13, 2000

(51) Int. Cl.⁷ .................................................. A61N 5/00
(52) U.S. Cl. ........................................ 600/1; 112/80.08
(58) Field of Search ........................... 112/80.08; 600/1, 600/3, 7, 585; 604/191; 606/130

(56) References Cited

U.S. PATENT DOCUMENTS

| | | | | |
|---|---|---|---|---|
| 4,897,076 A | * | 1/1990 | Puthawala et al. | 600/7 |
| 4,969,863 A | * | 11/1990 | Hooft et al. | 600/3 |
| 5,080,028 A | * | 1/1992 | Ingram | 112/80.08 |
| 5,584,815 A | * | 12/1996 | Pawelka et al. | 604/191 |
| 5,634,929 A | * | 6/1997 | Misko et al. | 606/130 |
| 5,769,779 A | * | 6/1998 | Alderson | 600/1 |
| 5,797,858 A | * | 8/1998 | Rourke | 600/585 |
| 5,997,462 A | * | 12/1999 | Loffler | 600/3 |
| 6,095,966 A | * | 8/2000 | Chornenky et al. | 600/3 |
| 6,248,101 B1 | * | 6/2001 | Whitmore et al. | 600/1 |
| 6,251,059 B1 | * | 6/2001 | Apple et al. | 600/3 |
| 6,398,709 B1 | * | 6/2002 | Ehr et al. | 600/3 |

* cited by examiner

*Primary Examiner*—Teresa Walberg
*Assistant Examiner*—Leonid M Fastovsky
(74) *Attorney, Agent, or Firm*—Rossi & Associates

(57) ABSTRACT

A pullback mechanism is provided that includes base block, a clamping retainer, and a sliding retainer. The clamping retainer preferably includes a clamping block and a mechanism for tightening the clamping block against the base block. The sliding retainer preferably includes a retainer carriage on which is mounted a clamping retainer and a mechanism for tightening the clamping retainer against the retainer carriage. In one preferred embodiment, the sliding retainer is mounted on a guide rail that is fixed to the base block. A pullback line attached at one end to the retainer carriage of the sliding retainer and at a second end to a movement imparting mechanism. A control unit controls the operation of the movement imparting mechanism to impart movement to the pullback line. In a further embodiment, a lead screw is provided on the base block and the sliding retainer is moveable coupled to the lead screw via a threaded mounting hole. In this embodiment, a flexible rotary connection is coupled to the lead screw and to a motion imparting mechanism. A control unit is provided to control the operation of the motion imparting mechanism.

19 Claims, 5 Drawing Sheets

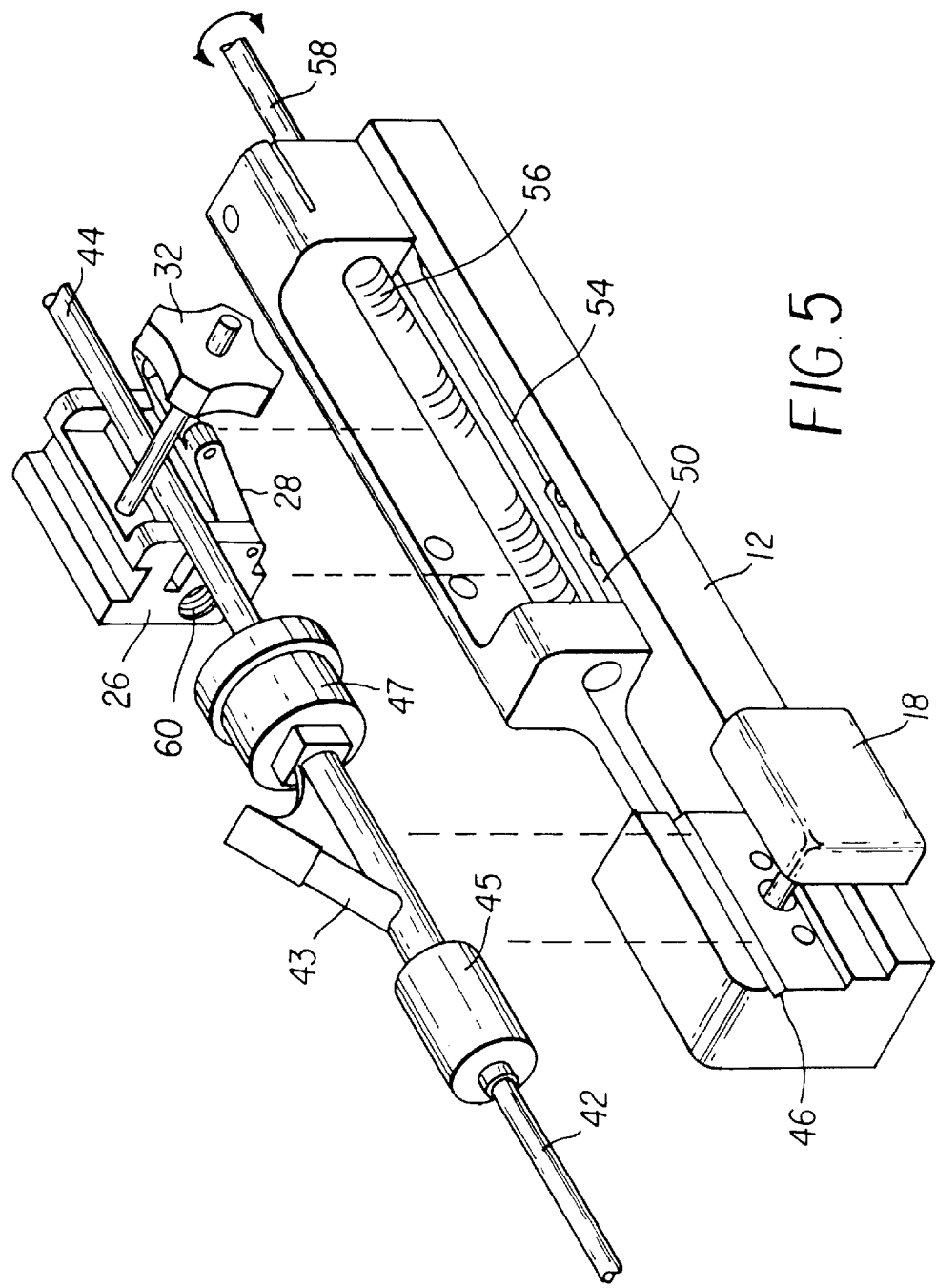

UNIVERSAL PULLBACK MECHANISM FOR IN-SITU TREATMENT DEVICE

FIELD OF THE INVENTION

The invention relates in general to mechanism for controlling the placement of treatment devices within the human body. More specifically, the invention relates to a pullback mechanism for use with in-situ treatment devices including flexible insertion devices that incorporate x-ray emitters.

BACKGROUND

Restenosis is a heart condition that afflicts 35%–50% of all people who undergo balloon angioplasty to improve blood flow in narrowed sclerotic arteries. The condition consists of a significant re-closing of the treated artery segment hours to several months after the procedure. As a result, the arterial lumen size is decreased and the blood flow downstream from the lesion site is impaired. Consequently, patients afflicted with restenosis must undergo an additional balloon angioplasty, and in some cases a coronary bypass surgery must be performed. Aside from the pain and suffering of these patients, recurrent stenosis is also a serious economic burden on society, with estimated expenses as high as 3.0 billion dollars per year in the United States economy alone.

Attempts to treat restenosis have been concentrated in both the pharmacological and medical device areas. While pharmacological solutions have been proven effective in treating only acute restenosis, a condition developing immediately after balloon angioplasty, some progress has been made with medical devices in the treatment of long term restenosis, a condition that develops up to a few months following balloon angioplasty. An example for such medical device is the stent. Stents can be inserted into an occluded artery to hold it open. Stents have been shown to prevent two of the three mechanisms that cause recurrent stenosis, namely, elastic recoil of the artery and negative remodeling of the arterial structure. The third mechanism, neointimal growth, consists of hyper-proliferation of smooth muscle cells from the lesion into the lumen and is not prevented by stents.

Ionizing radiation holds great promise for treating restenosis. Ionizing radiation serves to damage undesirable hyper-proliferating tissue and ultimately to prevent the hyper-proliferation of smooth muscle cells in the irradiated region. Research has shown that gamma and beta radiation delivered at the location of stenotic lesions effectively stop both animal and human intimal proliferation. The effective, yet non-hazardous, required dose to treat human restenosis is between seven and forty Gray (mjoule/gram), preferably a dosage greater than fifteen Gray measured two mm from the center of the radiation source that penetrates the artery wall at a two mm depth over the lesion length.

In view of the above, various methods have been proposed to provide ionizing radiation treatment. For example, radiation catheters, based on the use of radioactive sources such as beta–emitting $^{32}P$, $^{90}Sr/^{90}Y$, $^{188}W/^{188}Re$, beta+ emitting $^{48}V$ or gamma emitting $^{192}Ir$, are at various stages of development and clinical evaluation. The radioactive sources, in a variety of configurations, are introduced to the treatment sites using special radiation catheters and the radioactive source is placed at the treatment site for a predetermined time period as to deliver the proper radiation dose. Radioactive stents are also used as alternative delivery means, incorporating some of the above radioactive isotopes.

An additional approach to providing ionizing radiation treatment is through the use of an x-ray emitting energy transducer that is not radioactive. Co-pending and commonly assigned U.S. patent application Ser. No. 09/325,703 filed Jun. 3, 1999, and U.S. patent application Ser. No. 09/434,958 filed Nov. 5, 1999, describe miniaturized energy transducers that are coupled to flexible insertion devices to permit x-ray radiation treatment within the human body. Use of the miniaturized x-ray emitting energy transducer offers certain advantages with respect to intra vascular gamma and beta sources. These advantages are, but are not limited to, localization of radiation to the treatment site so that the treatment site may be irradiated with minimal damage to surrounding healthy tissue; reduction of hospital personnel risk due to exposure to radioactive materials; and minimization of the regulatory burden and additional costs that arise from the need to comply with nuclear regulatory requirements.

Regardless of the type of treatment device utilized, it is desirable to provide concise control of the placement and movement of the treatment device within the human body, thereby insuring that the treatment area is exposed to the correct dosage of radiation during the in-situ procedure. In cases in which the treatment device is provided as part of a catheter assembly, it has been proposed that a catheter pullback device be utilized to control the location and movement of the treatment device within the human body. International Publication Number WO 99/44687, for example, describes a system for delivering x-ray radiation including a catheter provided with an x-ray emitting device. The location of the catheter is controlled through the use of a reusable, customized pullback mechanism designed to work with a specific catheter device. Conventional pullback mechanisms, however, suffer from a number of disadvantages including: the need to sterilize the devices between procedures or alternatively to use sterile package, difficulties in locating the pullback mechanisms close to the entry point of the catheter due to their bulk and weight, and lack of interchangeability with conventional catheter devices and assemblies.

In view of the above, it is an object of the present invention to provide a pullback mechanism that provides precise location and movement of a treatment device within the human body. It is a further object of the present invention to provide a pullback mechanism of simple and lightweight design that can be easily handled during medical procedures and placed close to the entry point of a catheter. It is also an object of the present invention to provide an inexpensive pullback mechanism that can be disposed of after a procedure, thereby avoiding the problems associated with repeated sterilization or the need for sterile package. Still further, it is an object of the invention to provide a universal pullback mechanism that can be used with a variety of catheter assemblies and devices.

SUMMARY OF THE INVENTION

A pullback mechanism is provided that permits precise location and movement of a treatment device within the human body. The pullback mechanism is of simple and lightweight design that can be easily handled and located during medical procedures. Sterilization problems associated with conventional devices are avoided, as the pullback mechanism is disposable and therefore need not be repeatedly sterilized or repeatedly disposed within a sterile package for multiple uses. The pullback mechanism uses retainer mechanisms that can clamp and hold a variety of catheter assemblies and devices.

A pullback mechanism is provided that includes base block, a clamping retainer, and a sliding retainer. The clamping retainer preferably includes a clamping block and a mechanism for tightening the clamping block against the base block. The mechanism for tightening the clamping block against the base block preferably includes a clamping block bolt and a clamping block nut that is threaded over the clamping block bolt. The sliding retainer preferably includes a retainer carriage on which is mounted a clamping retainer and a mechanism for tightening the clamping retainer against the retainer carriage. As in the case of the clamping block, the mechanism for tightening the clamping retainer against the retainer carriage includes a retainer carriage bolt and a retainer carriage nut that is threaded on the retainer carriage bolt. The clamping retainer is coupled to the retainer carriage by a hinged connection, and includes a recess portion through which the retainer carriage bolt passes when the clamping retainer is opened.

In one preferred embodiment, the sliding retainer is mounted on a guide rail that is fixed to the base block. A pullback line attached at one end to the retainer carriage of the sliding retainer and at a second end to a movement imparting mechanism. A control unit controls the operation of the movement imparting mechanism to impart movement to the pullback line.

Additional preferred features include providing at least one of the clamping block and the base block includes a retaining groove and providing at least one of the retainer carriage and the hinged clamping retainer includes a retaining groove.

In addition, a mechanism for biasing the clamping retainer in a desired position can be employed if desired. The mechanism preferably includes a slide block located in a slot provided in the base block and coupled to the bottom of the sliding retainer, and a tension device coupled to the slide block.

In a further embodiment, a lead screw is provided on the base block and the sliding retainer is moveable coupled to the lead screw by via a threaded mounting hole. In this embodiment, a flexible rotary connection is coupled to the lead screw and to a motion imparting mechanism. A control unit is provided to control the operation of the motion imparting mechanism.

Further features and advantages of the invention will become apparent to those skilled in the art from the following detailed description of the preferred embodiments of the invention and the accompanying drawings.

BRIEF DESCRIPTION OF THE DRAWINGS

The invention will be described with reference to detailed descriptions of certain preferred embodiments thereof along with the accompanying drawings, wherein:

FIG. 5 is a partial exploded view of a disposable pullback mechanism in accordance with a further embodiment of the invention.

DETAILED DESCRIPTION OF THE PREFERRED EMBODIMENTS

Figure 1:
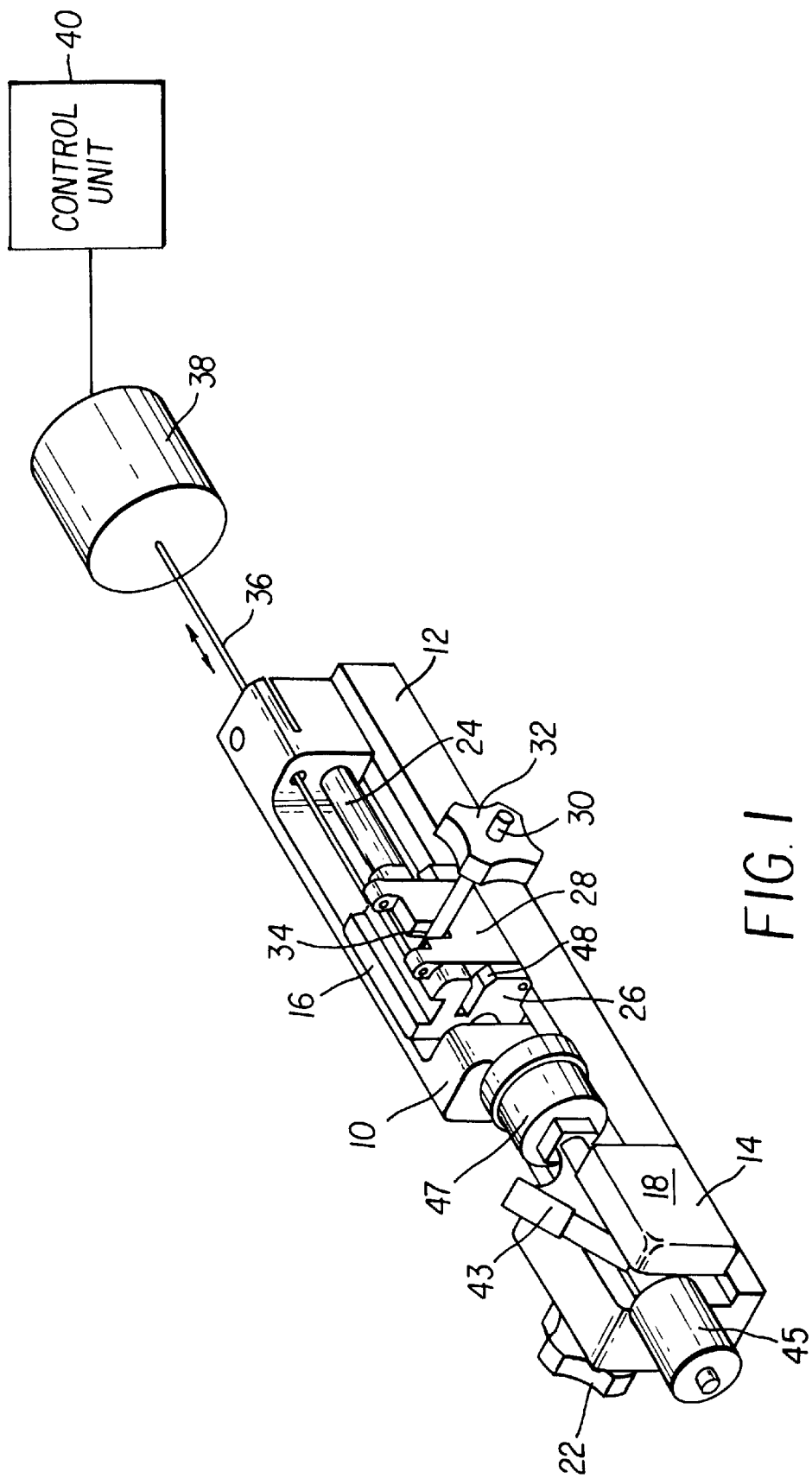
FIG. 1 is a side perspective view of a disposable pullback mechanism in accordance with an embodiment of the invention.
Figure 2:
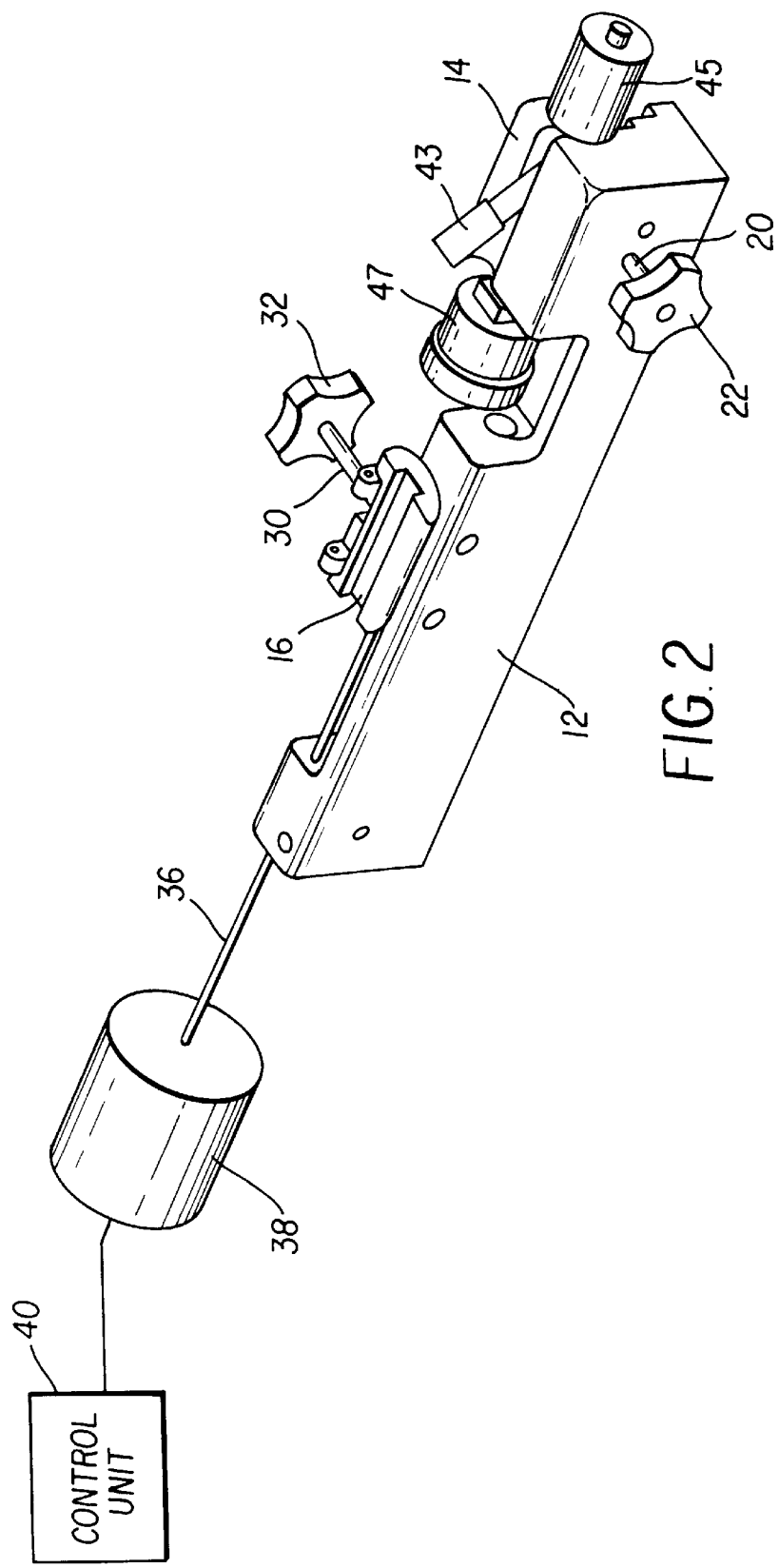
FIG. 2 is a side perspective view of a disposable pullback mechanism in accordance with the embodiment shown in FIG. 1.

A disposable pullback mechanism 10 in accordance with a preferred embodiment of the invention is shown in perspective views in FIGS. 1 and 2. The disposable pullback mechanism 10 includes a base block 12, a clamping retainer 14 and a sliding retainer 16. The clamping retainer 14 includes a clamping block 18 having a clamping block bolt 20 that passes through an opening in the base block 12. A clamping block hand nut 22 is threaded over the clamping block bolt 20, such that the clamping block 18 is drawn toward the base block 12 when the clamping block hand nut 22 is tightened. The sliding retainer 16 is mounted on a guide rail 24 that is fixed to the base block 12, such that the sliding retainer 16 can move freely over the guide rail 24 with respect to the base block 12. The sliding retainer 16 includes a retainer carriage 26 on which is mounted a hinged clamping retainer 28 and a retainer carriage bolt 30. A retainer carriage hand nut 32 is threaded on the retainer carriage bolt 30. The hinged clamping retainer 28 includes a recess portion 34 through which the retainer carriage bolt 30 passes, wherein the hinged clamping retainer 28 can be freely opened when the retainer carriage hand nut 32 is loosened to allow sufficient clearance, but is secured against the retainer carriage 26 when the retainer carriage hand nut 32 is tightened.

Movement is imparted to the sliding retainer 16 through the use of a pullback line 36 and a motor 38 under control of a control unit 40. The pullback line 36 is attached to the retainer carriage 26 of the sliding retainer 16 and to the motor 38. Activation of the motor 38 by the control unit 40 causes the pullback line 36 to move either forward or backward, which in turn causes the retainer carriage 26 to move forward or backward along the guide rail 24. The motor 38 can be a linear type motor, a stepper motor or any other type of motor or movement imparting mechanism that is capable of moving the pullback line 36 at the desired velocity or increments. Similarly, the control unit 40 can control the operation of the motor 38 in a variety of modes including the use of a preprogrammed sequence or based on feedback signals provided from a treatment mechanism.

During a treatment procedure, a guiding catheter 42 is inserted into the body of a patient. The guiding catheter 42 is provided with a rotatable hemostatic adaptor 45 mounted on a proximal end and a Y-connector 43 which is mounted on rotatable hemostatic adaptor 45. The Y-connector 43 is provided with a knob 47 that comprises a means for preventing blood or any other fluid leakage from the guiding catheter 42 during the operation of the pullback mechanism 10. Such means may include, for example, a hemastatic valve or any other means that can be urged into sealing engagement with a flexible insertion device 44 that is passed through the Y-connector 43 and positioned within the guide catheter 42. The sealing mechanism allows flexible insertion device 44 to move with respect to guiding catheter 42 and Y-connector 43, while the disposable pullback mechanism 10 is used to move the flexible insertion device 44 back and forth within the guide catheter 42 during the treatment procedure. The flexible insertion device 44 may include any device incorporating a treatment mechanism, for example a radioactive source or an x-ray emitting device, used for in-situ treatment of a condition within the patient's body, or it may be a diagnostic means such as an IVUS catheter. Specifically, the clamping block hand nut 22 is loosened to allow the Y-connector 43 to be placed between the clamping block 18 and the base block 12 as illustrated in FIGS. 1 and 2. As shown in greater detail in the partial exploded view shown in FIG. 3, at least one of the clamping block 18 and the base block 12 includes a V-shaped retaining groove 46 which assists in locating and maintaining the Y-connector 43 in a proper position. The retainer carriage hand nut 32 is also loosened to allow the hinged clamping retainer 28 to be lowered, so that the flexible insertion device 44 can be placed next to the retainer carriage 26. Preferably, at least one of the retainer carriage 26 and the hinged clamping retainer 28 also includes a V-shaped retaining groove 48 (see FIG. 1) which assists in locating and maintaining the flexible insertion device 44 in the correct position. The clamping block hand nut 22 is then tightened to hold the Y-connector 43 firmly within the clamping retainer 14. Similarly, the hinged clamping retainer 28 is closed and the retainer carriage hand nut 32 is tightened to firmly grasp the flexible insertion device 44 within the sliding retainer 16. The control unit 40 is then activated to control the operation of the motor 38 to move the pullback line 36 in either the forward or reverse direction as required.

Figure 3:
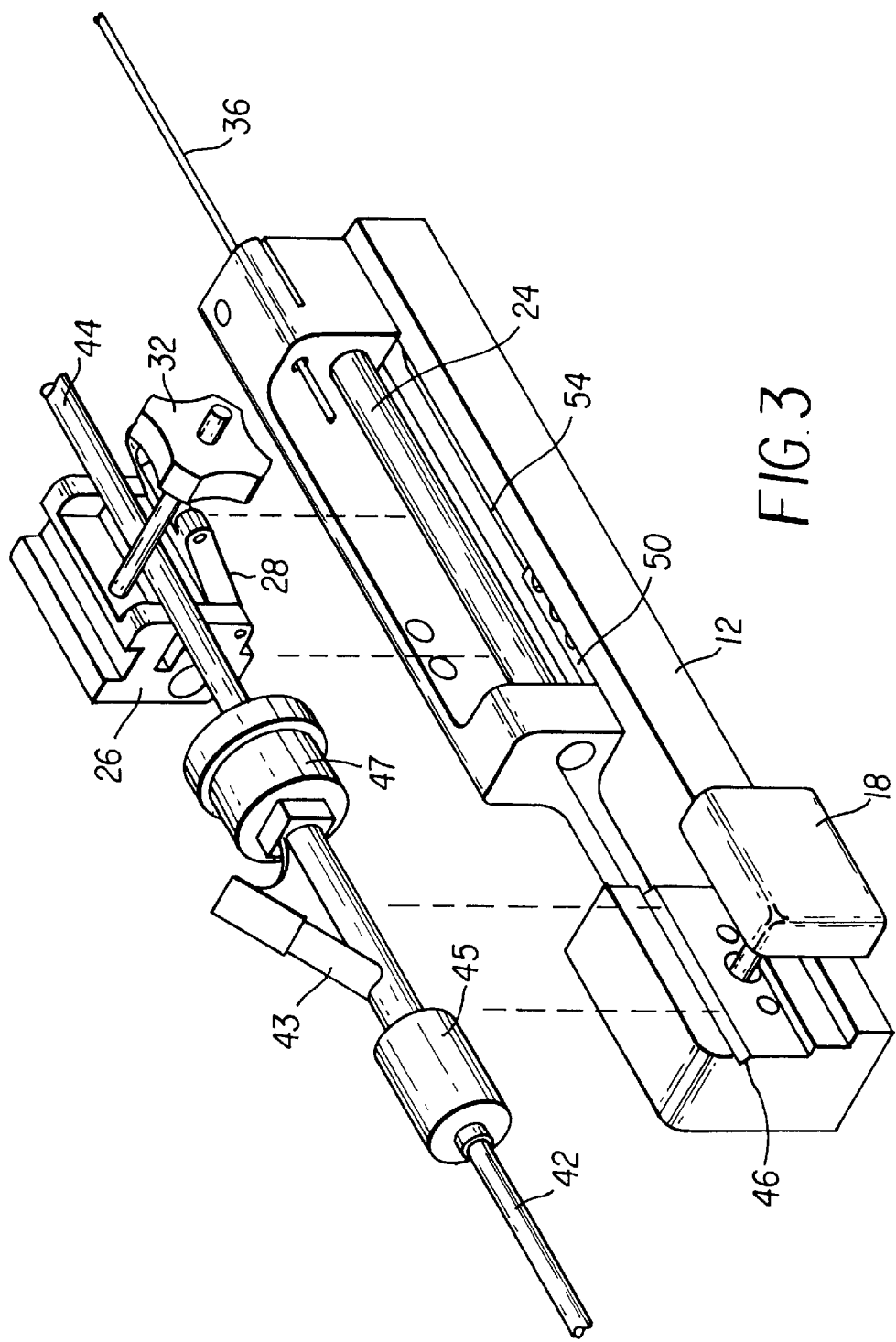
FIG. 3 is a partial exploded view of a disposable pullback mechanism in accordance with the embodiment shown in FIGS. 1 and 2.
Figure 4:
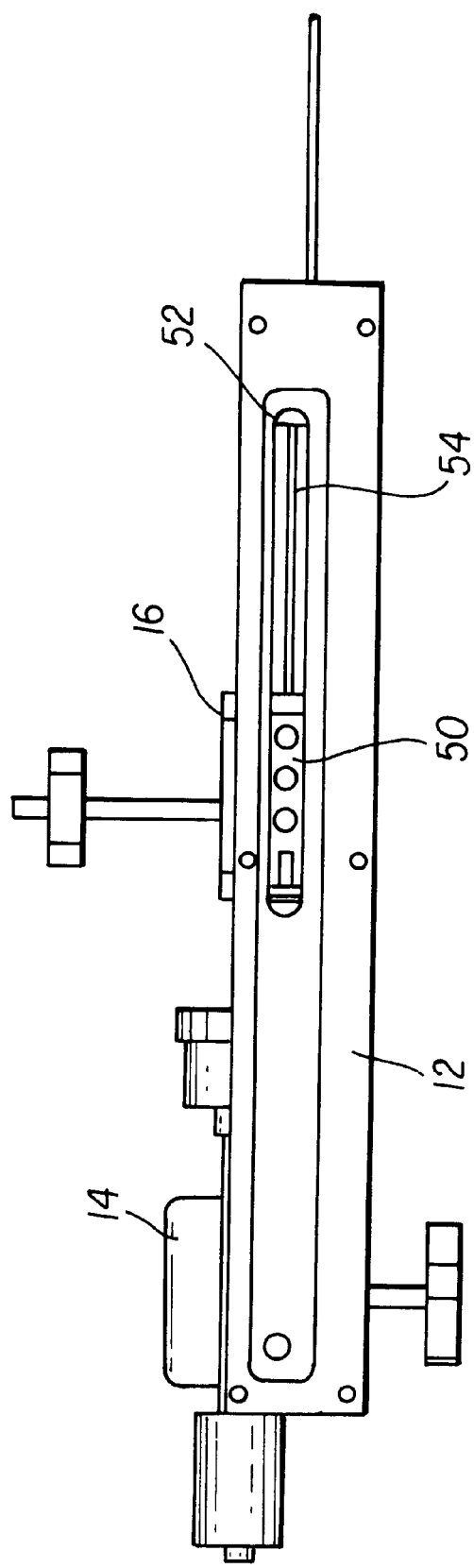
FIG. 4 is a bottom view of the disposable pullback mechanism in accordance with the embodiment illustrated in FIGS. 1–3.

Depending on the application, it may be preferably to bias the clamping retainer 14 in either a forward position or a reverse position. FIGS. 3 and 4 illustrate the use of a slide block 50 that is located in a slot 52 provided in the base block 12 and coupled to the bottom of the sliding retainer 16. A tension device 54, for example a spring or elastic band, is used to bias the slide block 50 in a desired position.

FIG. 5 illustrates a further preferred embodiment of the invention in which the guide rail 24 is replaced with a lead screw 56. In this embodiment, retainer carriage 26 includes a threaded mounting hole 60, such that rotation of the lead screw 56 causes the retainer carriage 26 to move back and forth along the lead screw 56. In this embodiment, the pull back line 36 is also eliminated and replaced with a flexible rotary connection 58 that is coupled to the motor 38. The motor 38 imparts a rotational motion to the flexible rotary connection 58, instead of a linear motion that was applied in the case of the pull back line 36, which in turn is imparted to the lead screw 56.

The pullback mechanism 10 of the present invention provides a number of advantages over conventional pullback mechanisms. In some conventional pullback mechanisms, the motor or drive mechanism is an integral part of the pullback mechanism, which adds to the weight and size of the pullback mechanism and rules out the possibility of making the mechanism disposable. In contrast, the motor 38 is separated from the pullback mechanism 10 of the present invention, which allows the pullback mechanism 10 to be of a lightweight and compact design. More importantly, the pullback mechanism 10 can be disposed of after use, thereby avoiding the problems associated with repeated sterilization or the need for sterile packing. Still further, the utilization of the clamping retainer 14 and sliding retainer 16 allows the inventive pullback mechanism 10 to be easily used with any type of conventional catheter system or flexible insertion device, as opposed to requiring a customized catheter specifically designed to fit with a customized pullback mechanism.

The invention has been described with reference to certain preferred embodiment therein. It will be understood, however, that modifications and variations are possible within the scope of the appended claims. It will also be understood that the clamping block 18 can be used to directly clamp guiding catheter 42 instead of an intermediate connection. Further, any type of securing mechanism can be used to secure the clamping block 18 and the clamping retainer 28 in position. These are just examples of a few possible variations that would fall within the scope of the appended claims.

What is claimed is:

1. A pullback mechanism comprising:
   a base block;
   a clamping retainer;
   a sliding retainer; and
   a pullback line attached to the retainer carriage of the sliding retainer.

2. A pullback mechanism as claimed in claim 1, wherein the clamping retainer includes a clamping block and a means for tightening the clamping block against the base block.

3. A pullback mechanism as claimed in claim 2, wherein the means for tightening the clamping block against the base block includes a clamping block bolt and a clamping block nut that is threaded over the clamping block bolt.

4. A pullback mechanism as claimed 1, wherein the sliding retainer is mounted on a guide rail that is fixed to the base block.

5. A pullback mechanism comprising:
   a base block;
   a clamping retainer; and
   a sliding retainer;
   wherein the sliding retainer includes a retainer carriage on which is mounted a retainer carriage clamping retainer and means for tightening the retainer carriage clamping retainer against the retainer carriage.

6. A pullback mechanism as claimed in claim 5, wherein the means for tightening the retainer carriage clamping retainer against the retainer carriage includes a retainer carriage bolt and a retainer carriage nut that is threaded on the retainer carriage bolt.

7. A pullback mechanism as claimed in claim 6, wherein the retainer carriage clamping retainer is coupled to the retainer carriage by a hinged connection.

8. A pullback mechanism as claimed in claim 7, wherein the retainer carriage clamping retainer includes a recess portion through which the retainer carriage bolt passes when the clamping retainer is opened.

9. A pullback mechanism as claimed in claim 1, wherein a first end of the pullback line is attached to the retainer carriage and a second end of the pullback line is coupled to a movement imparting mechanism.

10. A pullback mechanism as claimed in claim 9, further comprising a control unit coupled to the movement imparting mechanism, wherein the control unit controls the operation of the movement imparting mechanism to impart movement to the pullback line.

11. A pullback mechanism as claimed in claim 2, wherein at least one of the clamping block and the base block includes a retaining groove.

12. A pullback mechanism as claimed in claim 5, wherein at least one of the retainer carriage and the retainer carriage clamping retainer includes a retaining groove.

13. A pullback mechanism comprising:

a base block;

a clamping retainer;

a sliding retainer; and means for biasing the clamping retainer in a desired position.

14. A pullback mechanism as claimed in claim 13, wherein the means for biasing comprises a slide block located in a slot provided in the base block and coupled to the bottom of the sliding retainer, and a tension device coupled to the slide block.

15. A pullback mechanism comprising:

a base block;

a clamping retainer; and a sliding retainer;

wherein a lead screw is provided on the base block and the sliding retainer is moveable coupled to the lead screw.

16. A pullback mechanism as claimed in claim 15, wherein the sliding retainer is moveable coupled to the lead screw via a threaded mounting hole.

17. A pullback mechanism as claimed in claim 15, further comprising a flexible rotary connection coupled to the lead screw.

18. A pullback mechanism as claimed in claim 17, further comprising a motion imparting mechanism coupled to the flexible rotary connection.

19. A pullback mechanism as claimed in claim 18, further comprising a control unit coupled to the motion imparting mechanism.

* * * * *